United States Patent
Heinonen et al.

(10) Patent No.: US 6,694,969 B1
(45) Date of Patent: Feb. 24, 2004

(54) METHOD TO IMPROVE OXYGENATION IN SUBJECTS SUFFERING IMPAIRED OXYGENATION

(75) Inventors: Erkki Heinonen, Helsinki (FI); Pekka Meriläinen, Espoo (FI); Görel Nyman, Knivsta (SE); Marieann Högman, Alunda (SE)

(73) Assignee: Instrumentarium Corp., Helsinki (FI)

( * ) Notice: Subject to any disclaimer, the term of this patent is extended or adjusted under 35 U.S.C. 154(b) by 423 days.

(21) Appl. No.: 09/668,625

(22) Filed: Sep. 22, 2000

Related U.S. Application Data
(60) Provisional application No. 60/155,526, filed on Sep. 22, 1999.

(51) Int. Cl.$^7$ ............................................... A61M 15/00

(52) U.S. Cl. ........................... 128/200.24; 128/203.12; 128/204.23

(58) Field of Search ................. 128/200.24, 203.12, 128/204.23

(56) References Cited

U.S. PATENT DOCUMENTS

| | | | | |
|---|---|---|---|---|
| 5,062,423 A | * | 11/1991 | Matson et al. | 128/207.15 |
| 5,103,814 A | * | 4/1992 | Maher | 128/204.18 |
| 5,365,922 A | * | 11/1994 | Raemer | 128/204.23 |
| 5,388,575 A | * | 2/1995 | Taube | 128/204.23 |
| 5,396,882 A | * | 3/1995 | Zapol | 128/200.14 |
| 5,485,827 A | | 1/1996 | Zapol et al. | 128/200.14 |
| 5,522,381 A | * | 6/1996 | Olsson et al. | 128/203.12 |
| 5,531,218 A | * | 7/1996 | Krebs | 128/203.12 |
| 5,558,083 A | | 9/1996 | Bathe et al. | 128/203.12 |
| 5,570,683 A | * | 11/1996 | Zapol | 128/200.14 |
| 5,606,976 A | * | 3/1997 | Marshall et al. | 600/484 |
| 5,615,669 A | * | 4/1997 | Olsson et al. | 128/203.12 |
| 5,699,790 A | * | 12/1997 | Bathe et al. | 128/204.22 |
| 5,713,349 A | * | 2/1998 | Keaney | 128/204.23 |
| 5,732,694 A | * | 3/1998 | Bathe et al. | 128/203.12 |
| 5,765,548 A | * | 6/1998 | Perry | 128/200.24 |
| 5,765,558 A | * | 6/1998 | Psaros et al. | 128/207.14 |
| 5,839,433 A | * | 11/1998 | Higenbottam | 128/204.21 |
| 5,871,009 A | * | 2/1999 | Rydgren et al. | 128/203.12 |
| 5,887,611 A | * | 3/1999 | Lampotang et al. | 137/93 |
| 5,918,596 A | | 7/1999 | Heinonen | 128/204.21 |
| 6,019,100 A | * | 2/2000 | Alving et al. | 128/203.12 |

(List continued on next page.)

FOREIGN PATENT DOCUMENTS

| | | |
|---|---|---|
| DE | 43 25 319 | 4/1994 |
| EP | 834 332 | 4/1998 |
| EP | 872 254 | 10/1998 |
| EP | 878 208 | 11/1998 |
| EP | 879 612 | 11/1998 |
| WO | 98/44976 | 10/1998 |

OTHER PUBLICATIONS

Gerlach et al.: "Long-term inhalation with evaluated low doses of nitric oxide for selective improvement of oxygenation in patients with adult respiratory distress syndrome", Intensive Care Med (1993) 19:443–449.

(List continued on next page.)

*Primary Examiner*—Aaron J. Lewis
(74) *Attorney, Agent, or Firm*—Andrus, Sceales, Starke & Sawall, LLP

(57) ABSTRACT

A method for improving oxygenation in subjects having essentially healthy lungs, as evidenced by the absence of a diagnosis of lung disease or injury, but having reduced alveolar gas exchange area. This reduction may be caused by such acute circumstances as an unnatural body position, or may be, for example, chronic as caused by obesity. The method employs the administration of nitric oxide (NO) into the breathing gases of such subjects. NO provided to alveoli collapsing during expiration is small compared to those remaining open, thereby to provide net reduction in the shunt and thus an oxygenation improvement. This result may be gained either by precise control of the inspired NO concentration or by pulsed administration of the NO.

13 Claims, 3 Drawing Sheets

U.S. PATENT DOCUMENTS

| | | | | |
|---|---|---|---|---|
| 6,089,229 A | * | 7/2000 | Bathe et al. | 128/204.21 |
| 6,109,260 A | * | 8/2000 | Bathe | 128/203.12 |
| 6,142,147 A | * | 11/2000 | Head et al. | 128/204.21 |
| 6,164,276 A | * | 12/2000 | Bathe et al. | 128/202.22 |
| 6,325,978 B1 | * | 12/2001 | Labuda et al. | 422/84 |

OTHER PUBLICATIONS

Gerlach et al.: "*Time–course and dose–response of nitric oxide inhalation for systemic oxygenation and pulmonary hypertension in patients with adult respiratory distress syndrome*", Euro J. of Clinical Investigation (1993) 23: 449–502.

Benzing et al.: "*Hypoxic pulmonary vasoconstriction in non–ventilated lung areas contributes to differences in hemodynamic and gas exchange responses to inhalation of nitric oxide*", Anesthesiology (1997) 86: 1254–61.

A. Strandberg et al: "*Atelectasis during anaesthesia and in the postoperative period*", Acta Anaesthesiol. Scand. (Feb. 1986) 30:2, 154–8).

L. Tokic et al.: "*Lung collapse and gas exchange during general anesthesia: effects of spontaneous breathing, muscle paralysis, and positive end expiratory pressure*", Anesthesiology (Feb. 1997) 66:2, 157–67).

Brodsky: "*Morbid obesity*", Current Anaesthesia and Critical Care (1998) 9:249–254).

Young et al.: "*Effects of inhaled nitric oxide 10 ppm in spontaneously breathing horses anaesthetized with halothane*", British Journal of Anaesthesia, Aug. 1999).

* cited by examiner

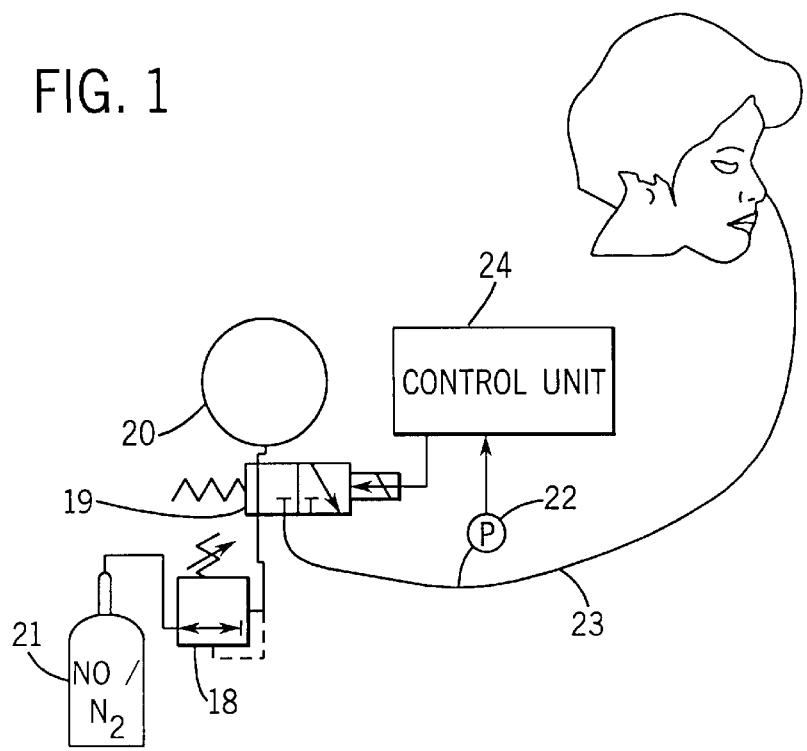
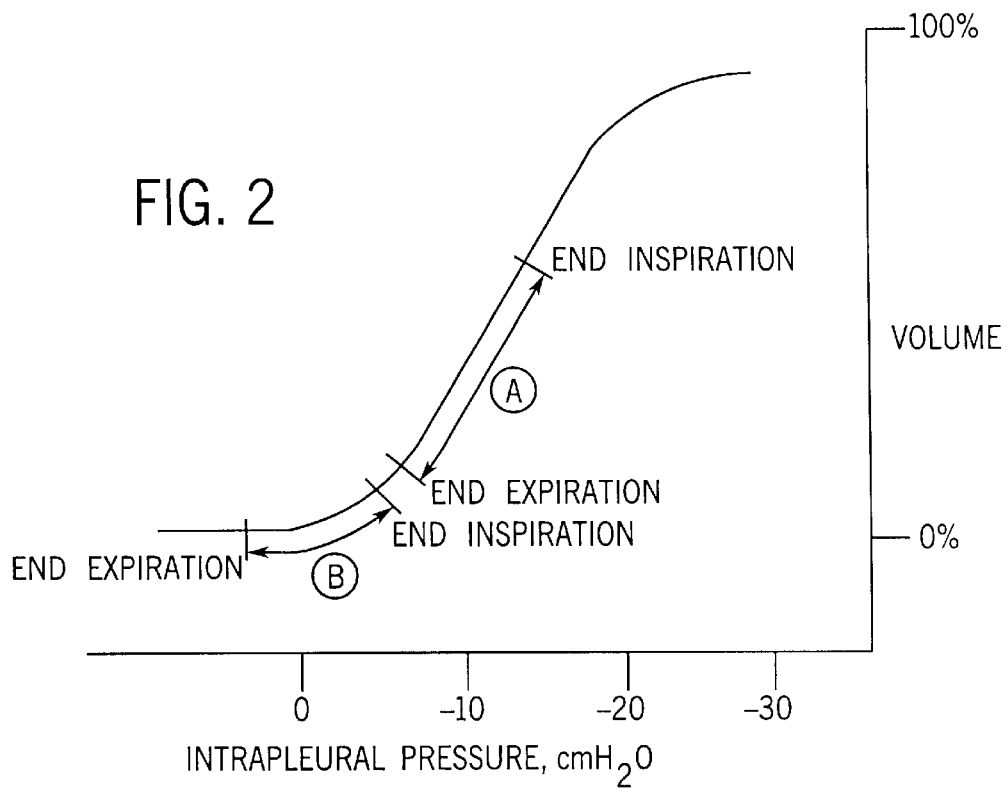

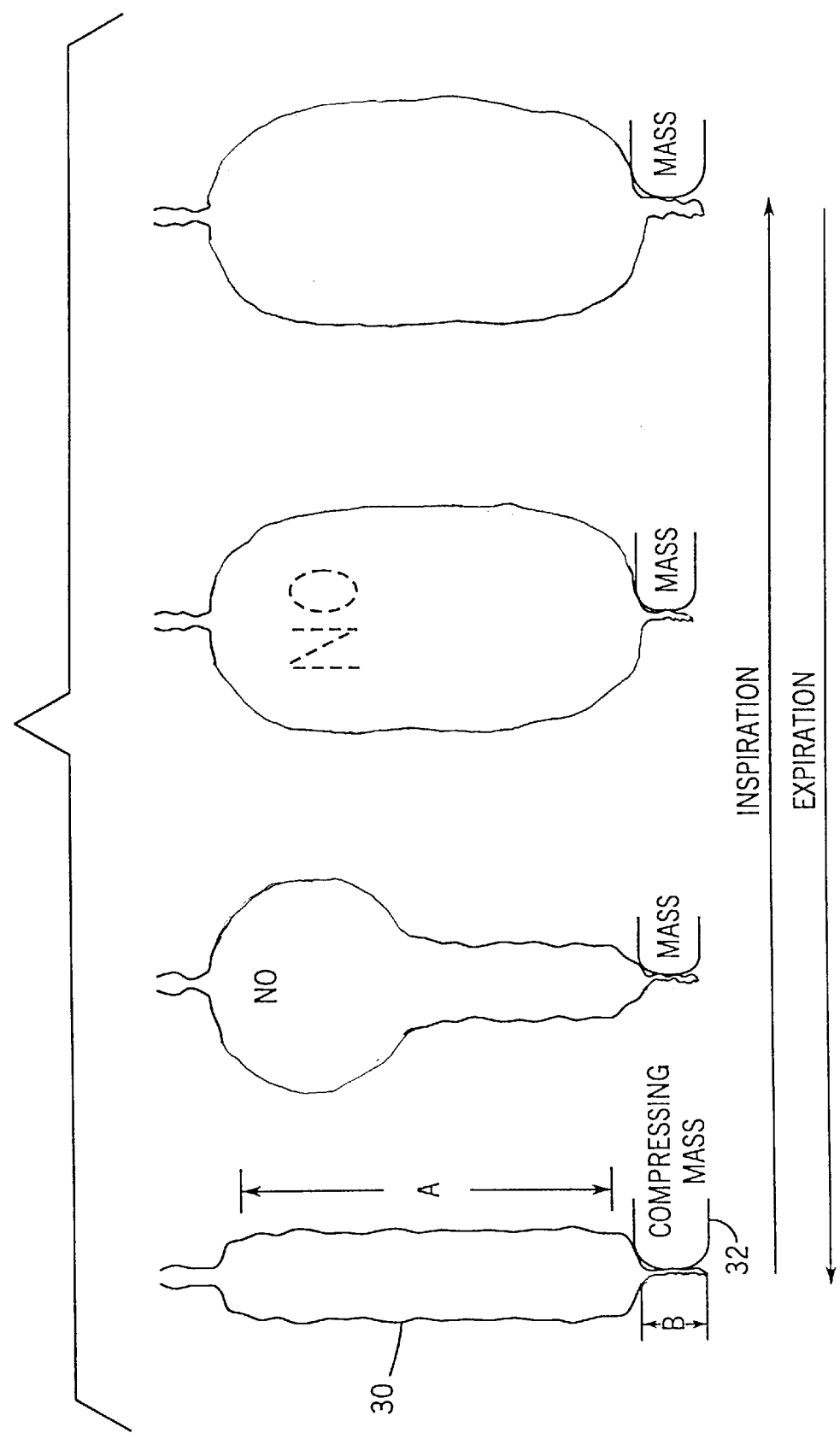

METHOD TO IMPROVE OXYGENATION IN SUBJECTS SUFFERING IMPAIRED OXYGENATION

CROSS REFERENCE TO RELATED APPLICATION

The present invention claims the priority of U.S. provisional application, Appln. No. 60/155,526, filed Sep. 22, 1999.

BACKGROUND OF THE INVENTION

Human and animal body metabolism uses oxygen and produces carbon dioxide. The required oxygen is received from the atmospheric air during respiration, in the course of which waste carbon dioxide is released. The gas exchange between the body and the environment takes place in the lung alveoli, where pulmonary blood capillaries are separated from the gas space in the lung in communication with the atmospheric air by only a thin membrane permeable for gases. The pulmonary blood flow passing through the alveoli equilibrates in gas partial pressure with the alveolar gas, resulting in blood oxygen uptake and carbon dioxide release. During each breath the alveolar blood gas concentration is changed as a result of the oxygen supplement and carbon dioxide removal. The blood transports the oxygen from the lungs to the sites of consumption and waste carbon dioxide from the sites of metabolism back to the lungs.

Blood flow rates through the lungs and perfusion pressure are regulated by the smooth muscle tension of the pulmonary capillaries. This regulation is mediated by endothelium derived nitric oxide. Insufficient local NO production increases smooth muscle tone. This results in pulmonary vasoconstriction and impaired blood flow or, alternatively, elevated pulmonary artery pressure. Pulmonary hypertension is present in various circumstances, such as pneumonia, traumatic injury, aspiration or inhalation injury, fat embolism in the lung, acidosis, inflammation of the lung, adult respiratory distress syndrome, acute pulmonary edema, acute mountain sickness, post cardiac surgery, acute pulmonary hypertension, persistent pulmonary hypertension of the newborn, prenatal aspiration syndrome, hyaline membrane disease, acute pulmonary embolism, heparinprotamine reactions, sepsis, or hypoxia (including that which may occur during one-lung anesthesia), as well as those cases of chronic pulmonary vasoconstriction which have a reversible component, such may result from chronic pulmonary hypertension, bronchopulmonary dysplasia, chronic pulmonary embolism, idiopathic or primary pulmonary hypertension, or chronic hypoxia due to chronic obstructive lung disease.

U.S. Pat. No. 5,485,827 discloses a method using inhaled nitric oxide (NO) useful for preventing or reversing acute pulmonary vasoconstriction, such as that arising from the foregoing injuries. A method for using NO gas also to achieve bronchodilatation and thereby improve the distribution of other agents administered by inhalation is also disclosed.

A special advantage of inhaled NO as a pulmonary vasodilator is its selectivity. NO is rapidly bound with blood hemoglobin, thus the free NO needed for mediating the vasodilatation is available selectively for the smooth muscles of the pulmonary capillaries only, and even more specifically, for the pulmonary capillaries adjacent ventilated alveoli. The pulmonary blood for alveoli which are not ventilated form a pulmonary shunt flow, since the non-ventilated alveoli are rapidly equilibrated with the pulmonary artery blood gases and no further gas exchange will take place. The pulmonary blood flow not participating in the gas exchange is thus called shunt flow. One reason for using inhaled NO therapy is to reduce the alveolar-arterial oxygen partial pressure difference for better oxygenation. The mechanism for this is reduction of the shunt. Administration of NO to ventilated alveoli dilates the pulmonary capillaries carrying blood for gas exchange. Capillaries in communication with the non-ventilated alveoli are constricted due to the low NO concentration. This results in blood perfusion redistribution towards the ventilated lung areas. When the portion of the pulmonary perfusion participating in the blood flow increases, the arterial oxygen partial pressure will increase, improving oxygenation.

Despite this well known mechanism, the published research results of inhaled NO for improving oxygenation have been limited. Examples of studies of oxygenation improvements are e.g. Gerlach et al.: "*Long-term inhalation with evaluated low doses of nitric oxide for selective improvement of oxygenation in patients with adult respiratory distress syndrome*", Intensive Care Med (1993) 19:443–449; Gerlach et al.: "*Time-course and dose-response of nitric oxide inhalation for systemic oxygenation and pulmonary hypertension in patients with adult respiratory distress syndrome*", Euro J. of Clinical Investigation (1993) 23: 449–502:, Benzing et al.: "*Hypoxic pulmonary vasoconstriction in non-verlated lung areas contributes to diff ences in hemodynamic and gas exchange responses to inhalation of nitric oxide*", Anesthesiology (1997) 86:1254–61. In all these, and other, published studies, NO has been administered to patients having a diagnosis of lung disease.

The NO delivery rate for improving oxygenation has both minimum and maximum limits making the oxygenation improvement clinically challenging. The loss of the oxygenation effect with increased doses is most likely traced back to the smooth muscle sensitivity. With increasing delivery, more NO diffuses to non- or poorly ventilated alveoli causing dilatation. This impairs the improvement in oxygenation seen prior to increasing the dose, as discussed by Gerlach in "Time-course . . . " The balance between improved and impaired gas exchange depends on lung status and is, therefore, individual for each patient. When the ventilation or lung performance is changing, most likely this balance is also affected.

Pulmonary shunt variation is very commonly present in healthy and sick lungs in various daily life and treatment conditions. Atelectasis, areas of the lung not participating in the gas exchange due to collapse of the alveoli, prevent normal oxygen delivery, and increases the pulmonary shunt. It has been pointed out that atelectasis is present during almost every anaesthesia (A. Strandberg et al: "*Atelectasis during anaesthesia and in the postoperative period*", Acta Anaesthesiol. Scand. (Feb. 1986) 30:2,154–8); L. Tokic et al: "*Lung collapse and gas exchange during general anesthesia: effects of spontaneous breathing, muscle paralysis, and positive end expiratory pressure*", Anesthesiology (Feb. 1997) 66:2, 157–67). In normal healthy subjects this atelectasis is not very significant due to the oxygenation reserve.

The severity of atelectasis will increase along with decrement of the oxygenation reserve. During artificial ventilation in anaesthesia and intensive care it is possible to increase the inhaled oxygen fraction and thereby increase the oxygenation reserve. In extensive collapse of lung, aeration with even 100% oxygen in the inhaled gases may not be sufficient. An example where the oxygenation reserve is endangered is horses experiencing anaesthesia in the unnatural supine position. The lungs, anatomically suited for the standing position, will be compressed by the body mass in the supine position. The lung volume can be reduced by as much as 50% and cause a pulmonary perfusion shunt of 20–50%. NO delivered to the inspired gas ca distribute the blood flow to ventilated areas and improve oxygenation.

Similar problems, which may in the worst case be chronic in nature, are encountered by humans having morbid obesity, i.e. twice the normal body weight, or 50 kg over the normal, or a body mass index over 40. In the supine position the lung functional residual capacity, FRC, is markedly reduced by the tissue mass restricting the lung volume. This may lead to impaired oxygenation and pulmonary shunt without any diagnosis of lung disease especially when sleeping when the lungs are squeezed by the body mass. Even worse, the diaphragm of obese people tends to assume a position which can be described as elevated when a person is standing, leading to a decrease in lung volume and increase in shunt. This may cause oxygenation problems even in normal daily life. The problem also occurs in anaesthesia or intensive care, and extends also to postoperative care where the restoration of normal pulmonary functions may take 4–5 hours (Brodsky: "*Morbid obesity*", Current Anaesthesia and Critical Care (1998) 9:249–254).

The compression of the lungs by the mass exerted on it may cause alveolar collapse during the time in which expiration occurs. The collapsed alveoli will open during the course of an inspiration when the lung opening pressure increases. The lung opening pressure required to open the lung increases towards the lowermost lung regions where the presence of the compressing mass of an obese person also increases, and more lung volume will be recruited along the progress of the inspiration. In spontaneous breathing this opening pressure is an underpressure in pleural cavity generated by breathing muscles of which the diaphragm is the most important. In artificial ventilation the opening pressure is overpressure in the lung gas space generated by the ventilator. At the beginning of expiration the lung opening pressure is relieved and the emptying of the lungs starts. The lung regions opened last during inspiration will close first at the beginning of expiration. This lung collapse will continue upwards from the lowermost lung region during expiration.

Due to the high diffusion capacity of alveolar NO into blood and the sensitivity of the capillary smooth muscle tone to the vasodilatory effect of NO, the NO has a rapid effect on the smooth muscle. Even the short period at the end of inspiration when the last alveoli will be opened before recollapse or bronchial reclosure at the beginning of expiration may be enough to dilate the capillaries. In the collapsed alveoli, the perfusion so enhanced does not participate in the gas exchange. The capillaries around the alveoli remaining open throughout the expiration will also dilate due to the inhaled NO. If the increased oxygenation in the latter is enough to overcome the ineffective dilatation around the collapsed alveoli a positive net oxygenation improvement will be obtained.

SUMMARY OF THE INVENTION

The current invention relates to a method for improving oxygenation in subjects having essentially healthy lungs, as evidenced by the absence of a diagnosis of lung disease or injury, but having reduced alveolar gas exchange area. This reduction may be caused by such acute circumstances as an unnatural body position, or may be, for example, chronic as caused by obesity. The method employs the administration of nitric oxide into the breathing gases of such subjects. NO provided to alveoli collapsing during expiration is small compared to those remaining open, thereby to provide net reduction in the shunt and thus an oxygenation improvement. This result may be gained either by precise control of the inspired NO concentration or by pulsed administration of the NO.

The inhalation NO delivery to the collapsing alveoli has to be small enough not to exert vasodilatation, whereas the delivery to the alveoli remaining open throughout inspiration and expiration has to be sufficient to create the dilatation. For an administration of NO taking place at constant inspired concentration, precise control of the delivery rate is required to limit the amount of NO delivered to collapsing lung areas yet to provide enough NO for the alveoli remaining open so as to get the net effect in the form of pulmonary shunt reduction and oxygenation improvement.

Alternatively, the pulse NO administration can be timed to occur in the first e.g. 30–70% of inspiration. Such administration avoids delivery into the last opening alveoli and thus dilatation of the capillaries associated with those alveoli. With pulsed administration, control of the NO delivery rate is less critical.

Various other features, objects, and advantages of the invention will be made apparent from the following detailed description and the drawings.

BRIEF DESCRIPTION OF THE DRAWINGS

FIG. 1 is a schematic diagram of apparatus suitable for carrying out the method of the present invention;

FIG. 2 is a graph relating lung volume to intrapleural pressure;

FIG. 3 is a simplified showing of the information contained in the graph of FIG. 2;

DETAILED DESCRIPTION OF THE PREFERRED EMBODIMENT

Figure 4:
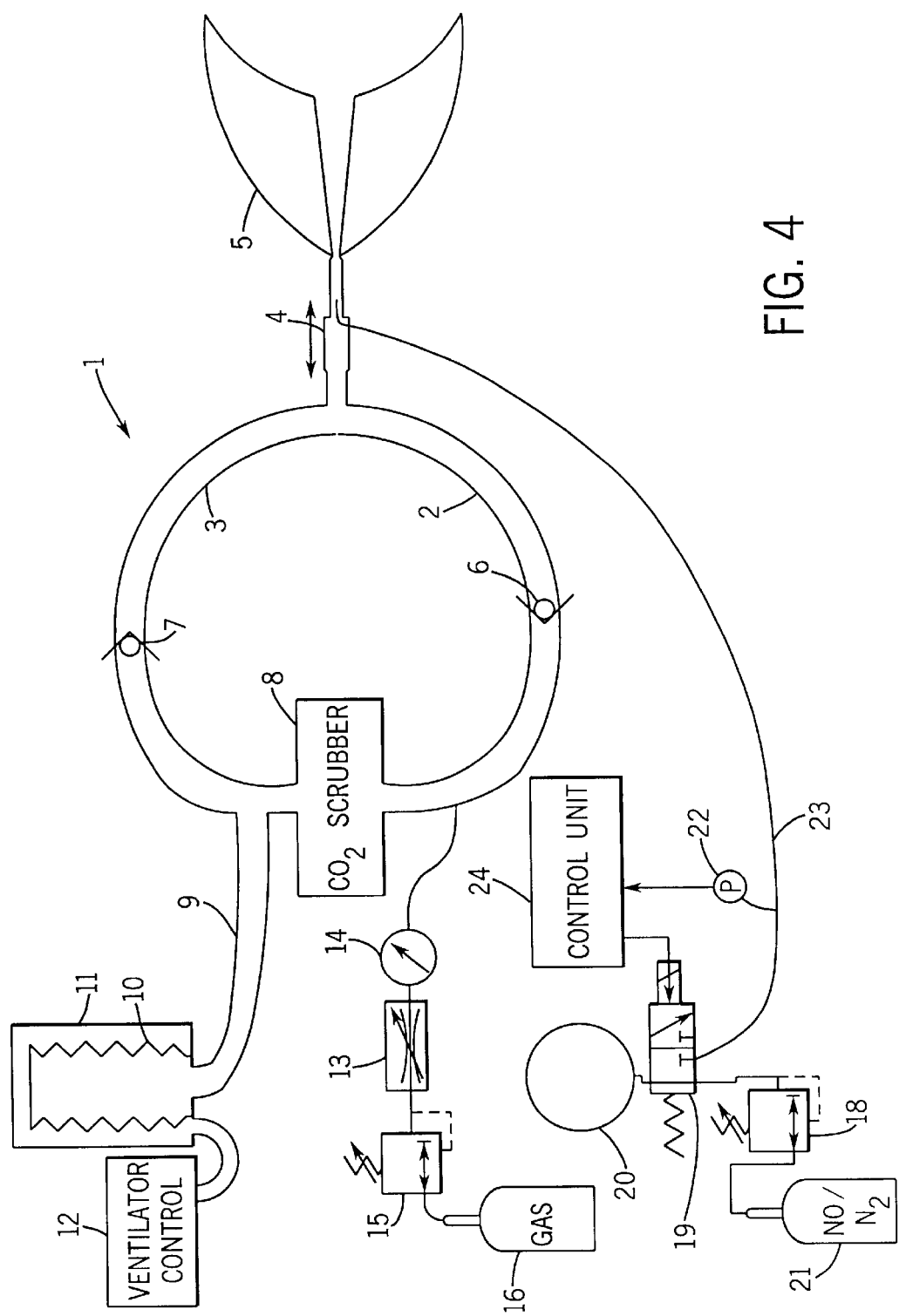
FIG. 4 and is a schematic diagram of alternative apparatus for carrying out the method of the present invention.

A device for pulsed NO administration is shown in FIG. 1. The NO from the supply 21 is conducted through a pressure regulator 18, regulating the supply pressure to an appropriate level, and through a delivery control valve 19 to a dosing chamber 20. The dosing chamber has a fixed known volume. When loading into fixed known volume at a pressure regulated by the pressure regulator 18, the amount of gas in the dosing chamber is known. For delivery, the control unit 24 activates the control valve 19 connecting the dosing chamber to the delivery line 23 and closing the connection between the NO supply and the dosing chamber. The gas from the dosing chamber will be exhausted until the dosing chamber pressure equilibrates with the environmental pressure. The gas delivered is thus the difference in the dosing chamber gas amount between the beginning and end of the delivery pulse. The dosing chamber volume depends on the volume to be delivered. As an example, the 50 ml pulse volume used in clinical trials with horses, could be generated with 1 bar regulator overpressure and 50 ml chamber volume, or alternatively 2 bar overpressure and 25 ml chamber volume. With fixed chamber volume, adjusting the regulated supply pressure can regulate the dose volume. Alternatively, the valve opening can be of fixed duration. For a subject breathing in the normal manner, the NO pulse may be delivered to the subject by a nasal cannula, or other suitable means.

The dose is administered through delivery line 23 to the nasal cannula. For synchronization of the pulse administration, the NO delivery device is equipped with a pressure sensor. Inspiration by the subject causes an under pressure in the spontaneous breathing. This pressure signal is transported through the delivery line to a pressure sensor 22. When the sensor dens triggering pressure conditions, the trol unit 24 activates the valve 19 for dose delivery. The same pressure sensor can monitor the delivery since the flow resistance of the delivery line causes a pressure increment at the measurement point. After the pulse, the valve 19 is deactivated reestablishing the connection between the NO supply and the dosing chamber for dosing chamber reload.

As noted above, the present invention is directed to the provision of NO to subjects having essentially healthy lungs but for various reasons are suffering from a lack of adequate oxygenation of the blood. Inadequate oxygenation is evidenced by a large alveolar-arterial oxygen partial pressure difference or by a low arterial oxygen partial pressure level. With respect to the alveolar-arterial oxygen partial pressure difference, a difference larger than 20 kPa is evidence of inadequate oxygenation. In normal human subjects, the difference is essentially zero. With respect to arterial oxygen partial pressures, a partial pressure of less than 10 kPa is definite evidence of inadequate oxygenation in humans, the normal level being 13 kPa when breathing air. The administration of NO can be based on a determination that one or both of these conditions exist in the subject.

FIG. 2 presents the volume change in different lung sections at various intrapleural pressures encountered in the course of spontaneous breathing. The designation A shows alveoli remaining open throughout the expiration and the designation B shows alveoli collapsing during expiration and opening during inspiration. The arrows in the designations indicate the range of volumetric movement of the respective alveoli in the volume-intrapleural pressure curve. The figure shows the temporary opening of the alveoli identified as B. The NO delivery into these alveoli should be limited below the amount needed for vasodilatation of the capillaries proximate to these alveoli, since during expiration there is no alveolar volume remaining for gas exchange, and the increased blood flow increases the shunt. The alveoli identified as A remain open throughout the breath cycle and should be provided NO sufficient for inducing the vasodilatation.

FIG. 3 shows the same information as FIG. 2 in simplified form in which the portion of a healthy lung 30 containing alveoli B is shown compressed by tissue mass 32. As inspiration proceeds from left to right in FIG. 3, breathing gases containing NO, for example as a pulsatile dose, inflate lung 30. The inflation commences with the upper portion of the lung, i.e. the portion containing alveoli A shown in FIG. 2. By the time the end of inspiration approaches, as in the right hand side of FIG. 3, the concentration of NO has been diluted by the inhaled breathing gases and/or removed by gas transfer in alveoli A, so that little or no NO remains as the compressed portion of the lung finally inflates. NO delivery to alveoli B is thus limited. FIG. 3 also shows the action of the lung upon expiration.

A device for pulsed NO administration is also disclosed in earlier patent of a co-inventor named in this application, U.S. Pat. No 5,918,596. An alternate delivery apparatus specifically designed for NO administration in pulses synchronously with the inspiration is presented in FIG. 4 in the setting of an anesthesia system.

A particular advantage of pulsed NO delivery is obtained when a rebreathing circuit of this type shown in FIG. 4 is used. NO reacts with oxygen forming nitrogen dioxide ($NO_2$). $NO_2$ is highly poisonous gas and the concentration should be kept below 2 ppm (OHSA limit for working environment). $NO_2$ formation rate depends on the reaction time available, the concentration of oxygen present and the square of NO concentration. Delivering NO as a short pulse synchronously with inspiration directs the NO into perfused alveoli. Due to the high diffusion constant of NO into blood, the alveolar NO is rapidly taken up, and only a minor fraction will be exhaled to the breathing circuit keeping the circuit concentration low, thus reducing the formation of $NO_2$. With constant inspired concentration delivery, NO is administered into anatomic dead spaces as well as the lungs. When used with a breathing circuit, all the dead space gas will be exhausted, increasing the breathing circuit NO concentration and thereby the $NO_2$ formation.

In the NO therapy system presented in FIG. 4, the patient breathing circuit 1 is comprised of inspiratory limb 2, expiratory limb 3, subject limb 4, one-way valves 6 and 7, $CO_2$ scrubber 8, and ventilator lime 9. The breathing circuit is of standard construction and connects the subject's lungs 5 with the ventilator connecting tube 9. The ventilator connecting tube 9 connects the breathing circuit to a bellows 10 into which the subject expires during expiration. The bellows may be located within a container 11 connected to ventilator control 12 for artificial ventilation of the subject. One way valves 6 and 7 direct the inspiration and expiration flows to the respective flow paths. The scrubber 8 removes the $CO_2$ from the expires gas during rebreathing. The $CO_2$ cleaned gas is supplied with fresh gas from a gas mixer comprising a fresh gas flow control 13 and metering 14 for controlling the gas flow from supply 16. The pressure regulator 15 reduces the supply pressure to an appropriate level for the flow control. The fresh gas supply may comprise multiple gas sources and may include an anaesthetic vaporizer. The dose is administered through delivery line 23 to the subject limb 4 of the breathing circuit. In the embodiment shown in FIG. 4, pressure sensor 22 senses the over pressure produced by bellows 10.

In a clinical trial of 6 horses anaesthetized with isoflurane in oxygen in supine position, NO pulse volumes of 3.6 $\mu$mol and 4.9 $\mu$mol were delivered for each inspiration both in spontaneous breathing and in artificial ventilation. The NO delivery was carried out in the manner described above in which the delivery of NO was limited in the alveoli collapsing during expiration and opening during inspiration due to the supine position of the horses. Following the delivery, the arterial oxygen partial pressure increased from mean 14.5 kPa (5.1 kPa standard deviation) to 28.1 kPa (11). The change in pulmonary shunt calculated from the arterial and venous oxygen contents with the shunt equation was from 32.2% (5.9) to 22.4 (6.0). The changes were statistically significant ($p<0.01$). In contrast to this, 10 ppm constant inspired concentration did not provide any improvement in another study (Young et al.: "*Effects of inhaled nitric oxide 10 ppm in spontaneously breathing horses anaesthetized with halothane*", Brifish Journal of Anaesthesia, Aug. 1999).

As noted above, FIGS. 1 and 4 show the pulsed administration of NO. The invention may be practiced using a constant NO concentration during inspiration. In such a case a gas flow control, similar to that shown as 13 in FIG. 4 may be provided between the pressure regulator for the NO supply and a delivery line to control the amount of NO supplied to the subject during inspiration.

It is recognized that other equivalents, alternatives, and modifications aside from those expressly stated, are possible and within the scope of the appended claims.

What is claimed is:

1. A method for improving oxygenation and reducing shunt perfusion in a lung of a subject, the lung having no diagnosis of injury, in which a first portion of alveoli of the lung are collapsed by compression from body organs during an expiratory phase of a respiratory cycle and during the initial portions of an inspiratory phase and are open in the terminal portions of the inspiratory phase, the lungs having a second portion of alveoli that are open during both the inspiratory and expiratory phases of the respiratory cycle, said method comprising the step of:

during inspiration of breathing gases by the subject, (a) delivering NO gas to the second portion of alveoli in an amount to cause vasodilatation of capillaries associated with such alveoli to improve blood oxygenation (b) while minimizing delivery of NO gas to the first portion of alveoli to an amount below that causing vasodilatation of capillaries associated with the first portion of alveoli to avoid increasing shunt perfusion in the lungs.

2. The method according to claim 1 wherein the step of the method is further defined as delivering the NO gas in a pulse dose in the inspired breathing gases of the subject and wherein at least one of the timing and duration of the pulse doses is controlled to achieve the desired delivery of the NO gas.

3. The method according to claim 3 wherein the step of the method is further defined as delivering the pulse dose during the first 70% of the time during which the subject is inspiring.

4. The method according to claim 3 wherein the step of the method is further defined as delivering the pulse dose during the first half of the time the subject is inspiring.

5. The method according to claim 1 wherein the step of the method is further defined as controlling the concentration of the NO gas in the breathing gases of the subject to a level, which when inhaled, will achieve the desired provision of the NO gas to the second and first alveolar portions of the lung.

6. The method according to claim 5 wherein the step of the method is further defined as continuously delivering NO gas into the breathing gases of the subject.

7. The method according to claim 6 wherein the step of the method is further defined as controlling the delivery rate of NO gas into the breathing gases of the subject.

8. The method according to claim 1 further defined as comprising the step of measuring the subject's alveolar-arterial oxygen partial pressure difference and as delivering NO gas when the alveolar-arterial oxygen partial pressure difference is above a predetermined threshold.

9. The method according to claim 8 further defined as delivering NO gas when the partial pressure difference is greater than 20 kPa.

10. The method according to claim 1 further defined as including the step of measuring the subject's arterial oxygen partial pressure and as delivering NO gas when the partial pressure is less than a predetermined threshold.

11. The method according to claim 10 further defined as delivering NO gas when the subject's arterial oxygen partial pressure is less than 10 kPa.

12. The method according to claim 1 wherein the method is further defined as carried out on an equine subject in a supine position.

13. The method according to claim 1 wherein the method is further defined as carried out on an obese human subject whose obesity reduces the functional residual capacity of the lungs of the subject.

\* \* \* \* \*